United States Patent [19]

Kikuchi et al.

[11] Patent Number: 4,891,483

[45] Date of Patent: Jan. 2, 1990

[54] HEATING APPARATUS FOR HYPERTHERMIA

[75] Inventors: Makoto Kikuchi, Mitaka; Shinsaku Mori, Tokyo; Yoshio Nikawa, Tokyo; Takashige Terakawa, Tokyo, all of Japan

[73] Assignee: Tokyo Keiki Co. Ltd., Tokyo, Japan

[21] Appl. No.: 878,327

[22] Filed: Jun. 25, 1986

[30] Foreign Application Priority Data

Jun. 29, 1985 [JP] Japan .................................. 60-143555
Jun. 29, 1985 [JP] Japan .................................. 60-143559
Jun. 29, 1985 [JP] Japan .................................. 60-143560

[51] Int. Cl.⁴ ............................................... A61N 5/00
[52] U.S. Cl. ....................... 219/10.55 A; 219/10.55 R; 128/804; 128/399
[58] Field of Search ................. 219/10.55 A, 10.55 F, 219/10.55 R, 10.55 M; 128/804, 399, 422

[56] References Cited

U.S. PATENT DOCUMENTS

| | | | |
|---|---|---|---|
| 3,077,195 | 2/1963 | Fölsche | 128/404 |
| 3,329,148 | 9/1965 | Kendall | 128/804 |
| 3,939,901 | 2/1976 | Cieszko | 165/1 |
| 4,108,147 | 8/1978 | Kantor | 128/404 |
| 4,140,130 | 2/1979 | Storm, III | 128/404 |
| 4,204,549 | 5/1980 | Paglione | 128/804 |
| 4,228,809 | 10/1980 | Paglione | 128/804 |
| 4,282,887 | 8/1981 | Sterzer | 128/804 |
| 4,341,227 | 7/1982 | Turner | 128/804 |
| 4,397,313 | 8/1983 | Vaguine | 128/399 |
| 4,397,314 | 8/1983 | Vaguine | 128/399 |
| 4,403,618 | 9/1983 | Turner et al. | 128/804 |
| 4,446,874 | 5/1984 | Vaguine | 128/804 |
| 4,462,412 | 7/1984 | Turner | 128/804 |
| 4,530,358 | 7/1985 | Forssmann | 128/328 |
| 4,586,516 | 5/1986 | Turner | 128/804 |
| 4,589,424 | 5/1986 | Vaguine | 128/804 |
| 4,690,156 | 9/1987 | Kikuchi | 128/804 |

FOREIGN PATENT DOCUMENTS

| | | |
|---|---|---|
| 0111386 | 6/1984 | European Pat. Off. . |
| 1440333 | 4/1969 | Fed. Rep. of Germany . |
| 2060923 | 7/1971 | Fed. Rep. of Germany . |
| 2648908 | 5/1978 | Fed. Rep. of Germany . |
| 0028338 | 3/1977 | Japan . |
| WO88/01851 | 3/1988 | PCT Int'l Appl. .................. 128/804 |

OTHER PUBLICATIONS

"A Localized Current Field . . ." by Astrahan et al, Med. Phys. 9 (3), pp. 419–424, May/Jun. 1982.
NASA Technical Brief, p. 59, Spring 1980.
Book: "Hyperthermia in Cancer Therapy" by Storm, G. K. Hull Med. Pub., 1983.
*Microwaves*, Oct. 1976, p. 14.
"A Microwave System . . ." by Magin, IEEE Transactions Microwave Theory and Technology, MIT-27, No. 1, pp. 78–83, Jan. 1979.
"Techniques . . . Hyperthermia . . . Carcinoma" by Robinson et al. IEEE Transactions, Microwave Theory and Technology, MIT-26, No. 8, pp. 546–549, Aug. 1978.

*Primary Examiner*—A. D. Pellinen
*Assistant Examiner*—Leon K. Fuller
*Attorney, Agent, or Firm*—Sandler & Greenblum

[57] ABSTRACT

The applicator used in this invention functions as an antenna for delivering electromagnetic energy into a living body. The applicator is supported by a supporting mechanism through a supporting device. The applicator can move to and stop at a position through the action of this supporting mechanism. A cooling section is provided on the contact surfaces of the applicator and the living body so as to protect normal cells on the surface of living body. This cooling section is additionally provided with a coolant circulating device, which enables to continuously perform hyperthermia for a long period of time. The coolant circulating device has a pressure reducing mechanism to counter the fluctuations in fluidal pressure, and further, provided with a deaerating device for preventing the air from stagnating therein. Furthermore, in the heating apparatus for hyperthermia as disclosed in this invention, the supporting mechanism, and electromagnetic wave producing source and a general control section are separate from one another, thereby facilitating the use of the apparatus.

18 Claims, 14 Drawing Sheets

HEATING APPARATUS FOR HYPERTHERMIA

BACKGROUND OF THE INVENTION

1. Field of the Invention

This invention relates to a heating apparatus for hyperthermia, and more particularly to a heating apparatus for hyperthermia for locally heatingly treating a predetermined portion of a living body by use of electromagnetic waves.

2. Description of the Prior Art

In recent years, heating treatment methods (or referred to as "hyperthermia") have been highlighted, and particularly, such research reports have been successively submitted that, for example, a malignant tumor is continuously heated at about 43° C., for one or two hours, and the above treatment is repeated in preset cycles, whereby the regenerating function of cancer cells is impeded, and simultaneously, most of the cancer cells can be killed (MICROWAVES, October, 1976 issue, page 14). The heating treatment of the type described includes general heating and local heating. Out of these, as the locally heating methods for selectively heating the cancer system and thereabout, there are proposed a method by use of electromagnetic waves, another method by use of electromagnetic induction, a further method by use of ultrasonic waves, etc.

On the other hand, heretofore, the inventors of the present invention have proposed and proceeded with studies on the effectiveness in the case of heatingly treating a cancer in a deep portion of a living body by use of electromagnetic waves. In this case, as for an applicator for heating to deliver the electromagnetic waves into the living body, the inventors have, heretofore, adopted a technique of equipping an electromagnetic lens for the necessity of focusing energy of electromagnetic waves. More specifically, as shown in FIG. 1, an applicator 1 includes: a case body 3 functioning as a waveguide; a feeding section 2 provided on one end portion of the case body 3; and an electromagnetic lens section 4 provided on the other end portion of the case body 3. A solid cooling plate 5 for preventing the surface of living body from being overheated is mounted to an output stage of the electromagnetic lens section 4, and this solid cooling plate 5 may be cooled by a coolant liquid.

However, the above-described conventional example has the following disadvantages.

(1) When the applicator is brought into contact with the living body, a shift in position tends to occur due to the external vibrations.

(2) Air bubbles are produced in the coolant liquid at the applicator portion. The air bubbles form the obstruction, whereby an output of electromagnetic waves is lowered.

(3) The applicator tends to be damaged due to the fluctuations in fluidal pressure of the coolant.

(4) It is difficult to feed the coolant during operation because of the circulation of the coolant in a closed circuit.

(5) Because the applicator, an electromagnetic wave output source and a control section are formed integrally with one another, the apparatus as a whole is rendered large in size and heavy in weight, thus making the handling thereof troublesome.

SUMMARY OF THE INVENTION

It is an object of the present invention to provide a heating apparatus for hyperthermia, capable of efficiently applying electromagnetic energy to a cancer system in a living body by use of an electromagnetic lens for a predetermined period of time, to thereby perform local heating.

It is another object of the present invention to prevent a shift in position on the contact surface of the applicator with the living body due to the external vibrations and the like during performing hyperthermia.

It is a further object of the present invention to make a cooling mechanism mounted to the applicator function effectively.

It is a still further object of the present invention to provide a construction wherein the apparatus as a whole is easy in handling, so that the preparation for performing hyperthermia can be made quick and easy.

DETAILED DESCRIPTION OF THE INVENTION

The First Embodiment

The first embodiment of the present invention will hereunder be described with reference to FIGS. 2 to 14.

Figure 1:
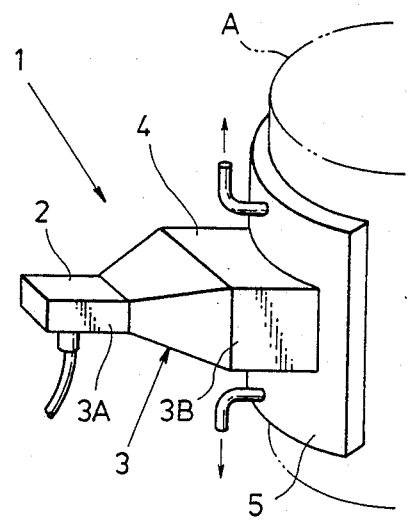
FIG. 1 is an explanatory view showing the conditions of use of the applicator in a conventional example.
Figure 2:
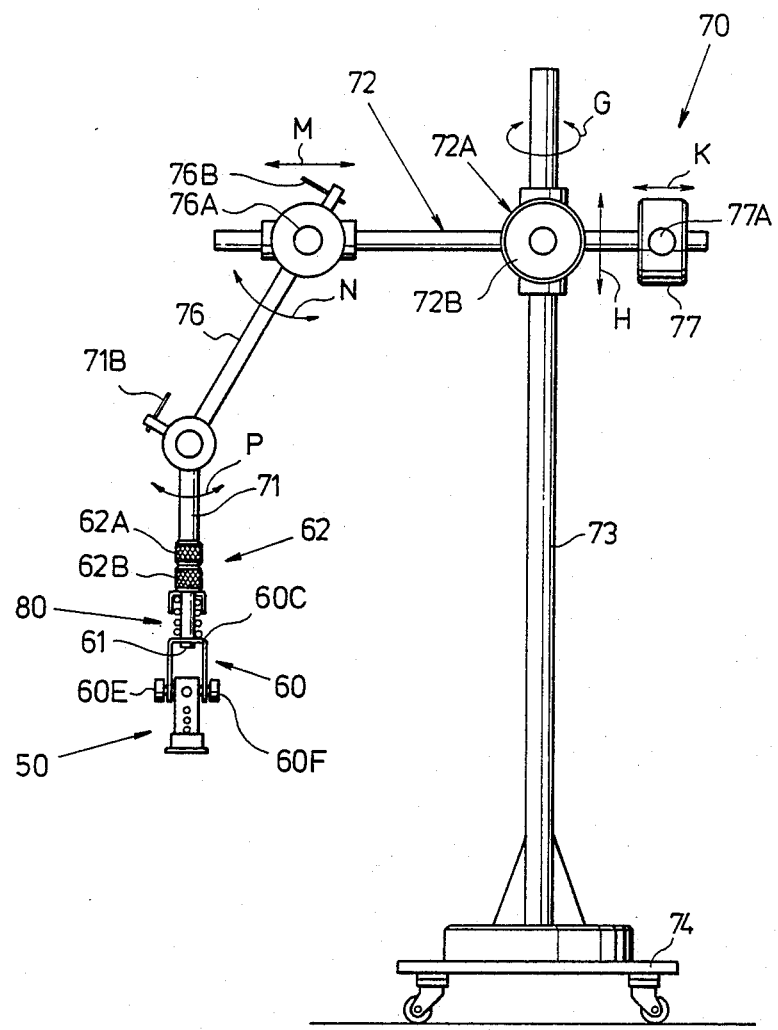
FIG. 2 is a front view showing a supporting mechanism in a first embodiment of the present invention.

First, in FIG. 2, designated at 50 is an applicator, 60 applicator holding means and 70 a supporting mechanism.

Figure 3:
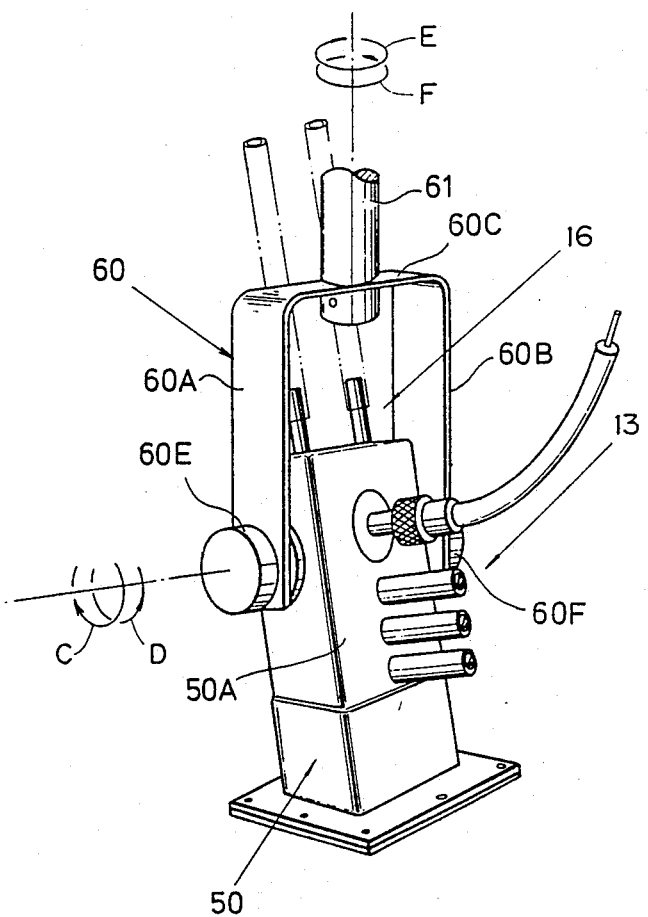
FIG. 3 is an enlarged perspective view showing an applicator means portion.

The applicator 50 is erectingly and rotatably engaged with the applicator holding means 60 through, engaging knobs 60E and 60F shown in FIGS. 2 and 3. Arrows C and D indicate directions of rotation in that case. In this case, the central portions of the engaging knobs 60E and 60F are extended inwardly and formed at ends thereof with threaded portions, not shown, respectively. These threaded portions extend through through-holes, not shown, of U-shaped bent end portions 60A and 60B of the applicator hoding means 60, and then, threadably coupled to threaded holes 10K of engageable pieces 10G and 10H (Refer to FIG. 7) provided at opposite sides of the applicator 50. Consequently, the applicator 50 is solidly secured to the applicator holding means 60 through the action of the engaging knobs 60E and 60F thereof in such a manner that the opposite sides of the applicator 50 is clamped by the bent end portions 60A and 60B of the applicator holding means 60.

Because of this, when the engaging knobs 60E and 60F are untightened, the applicator 50 can freely rotate in the aforesaid directions C and D. When the engaging knobs 60E and 60F are tightened as necessary, the applicator 50 can be fixed at a desirable inclined position.

Figure 5:
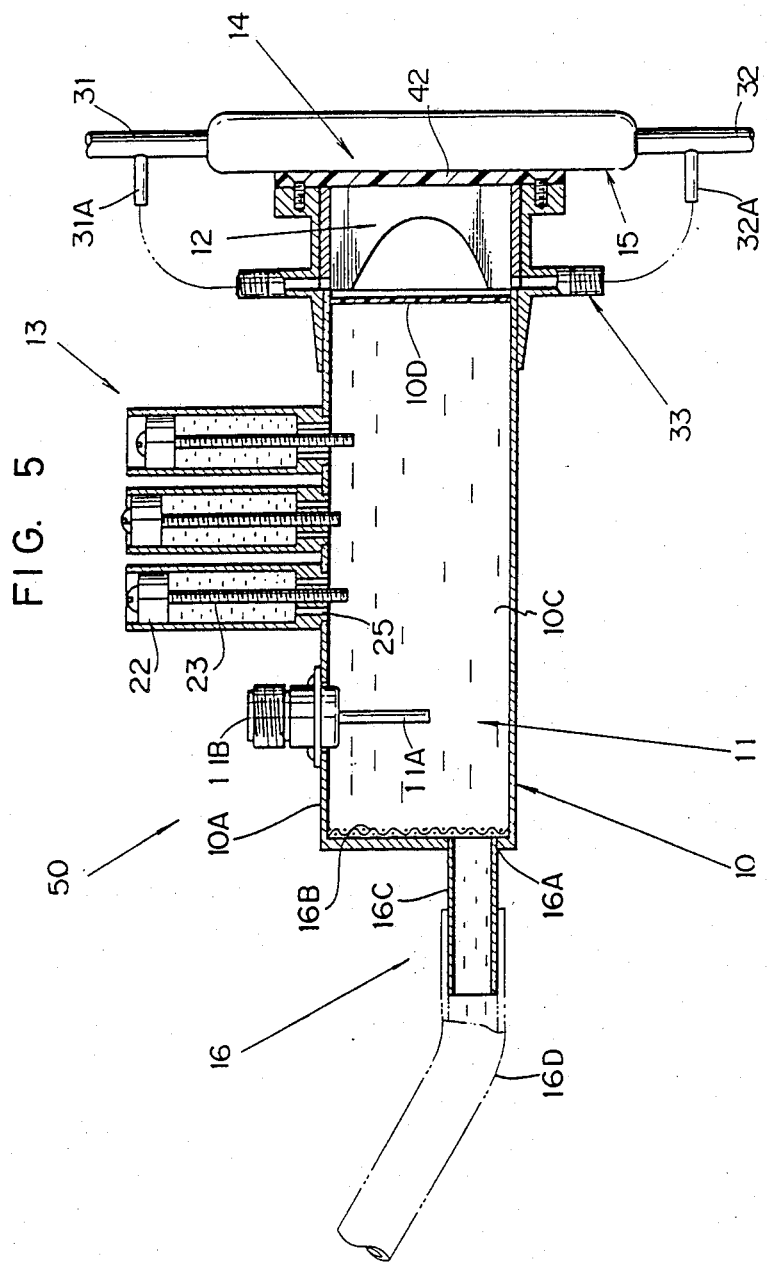
FIG. 5 is a sectional view showing an example of the applicator a portion of FIG. 2, including water feed guide.
Figure 6:
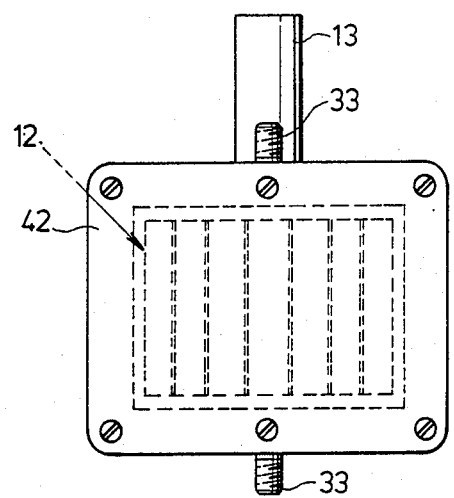
FIG. 6 is a right side view showing the case where a surface cooling mechanism in FIG. 5 is removed.
Figure 7:
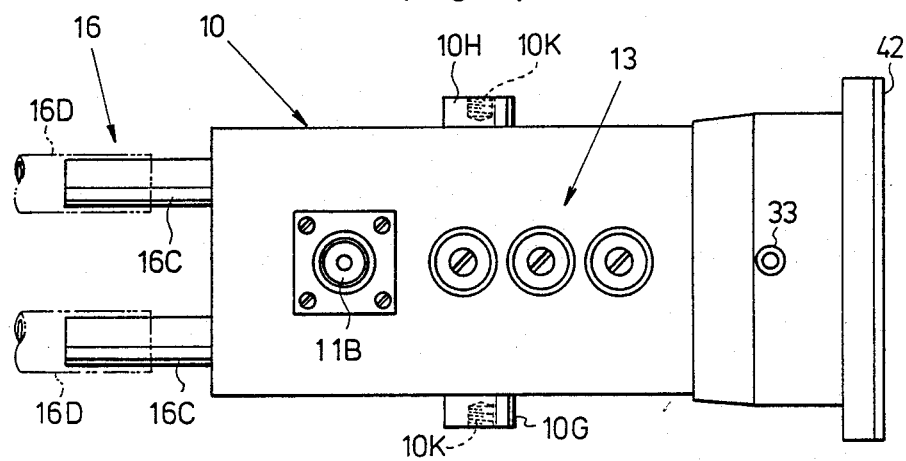
FIG. 7 is a plan view of FIG. 5.

More specifically, the applicator 50 is constructed as shown in FIGS. 5 to 10. In these drawings, denoted at 10 is a case body functioning as a waveguide. As apparent from FIGS. 5 to 7, this case body 10 is of a box form, provided at one end portion thereof with an electromagnetic wave feeding section 11 and at the other end portion with an electromagnetic lens section 12, and a stub tuner mechanism 13 for matching the electromagnetic waves is provided therebetween. Further, the right end portion of the electromagnetic lens section 12 in FIG. 5 forms an electromagnetic wave radiating section 14, which is additionally provided with a surface cooling mechanism 15 for the surface of living body in a manner to cover the electromagnetic wave radiating end section 14 from the outside for use as shown in FIG. 5.

The electromagnetic wave feeding section 11 includes: a feeding section waveguide 10A forming a portion of the case body 10; a driven antenna 11A projected to the central portion of this feeding section waveguide 10A; and a concentric connector 11B connected to this driven antenna 11A, being of a spindle shape, for the electromagnetic waves. With this arrangement, the electromagnetic waves delivered through the concentric connector 11B are efficiently introduced into the case body 10.

The feeding section waveguide 10A is filled up with insulating oil (hereinafter referred to briefly as "oil") 10C being low in attenuation of the electromagnetic waves, and further, includes a portion where the stub tuner mechanism 13 is provided. Designated at 10D is an oil sealing partition plate formed of a dielectric member, for sealing the oil 10C.

In this embodiment, as the stub tuner mechanism 13, one, in which a set of three stubs arranged on one and the same line at regular intervals, are used. In this stub tuner mechanism 13, respective threaded members 23 functioning as the stubs for matching reflective waves are rotated, whereby the threaded members 23 are appropriately projected into the case body 10, so that required matching can be achieved. Denoted at 22 is a piston member for sealing, and 25 a flow port for the movement of the oil 10C due to the reciprocatory motion of the piston member 22.

Furthermore, in order to smooth such flow of the oil 10C as described above, i.e. the reciprocatory motion of the piston member 22 and to permit the filler oil to thermally expand due to the heating of the case body 10 caused by the continuous use, an oil escaping mechanism 16 is provided in a portion of the feeding section waveguide 10A. In this embodiment, this oil escaping mechanism 16 includes: through-holes 16A and 16A (Refer to FIG. 5) formed at a predetermined interval at two positions on the feeding section waveguide 10A; a metal screen 16B having a relatively fine mesh and provided for covering the through-holes 16A from the inside; guide tubes 16C and 16C connected to the through-holes 16A, respectively; and relatively soft oil escaping tubes 16D and 16D connected to the guide tubes 16C and 16C and extending upwardly. Here, the metal screen 16B constitutes a portion of a side surface of the electromagnetic feeding section 11. As far as any one equals to this in function, for example, the metal screen 16B may be replaced by an inner wall of the electromagnetic feeding section 11, which is formed with a multiplicity of small holes, a plate-shaped metal member having a numerous small through-holes or the like.

Furthermore, the surface cooling mechanism 15 used in the electromagnetic wave radiating end section 14 of the case body 10 is formed to provide a flat shape to efficiently cool the surface of a heated portion.

Figure 4:
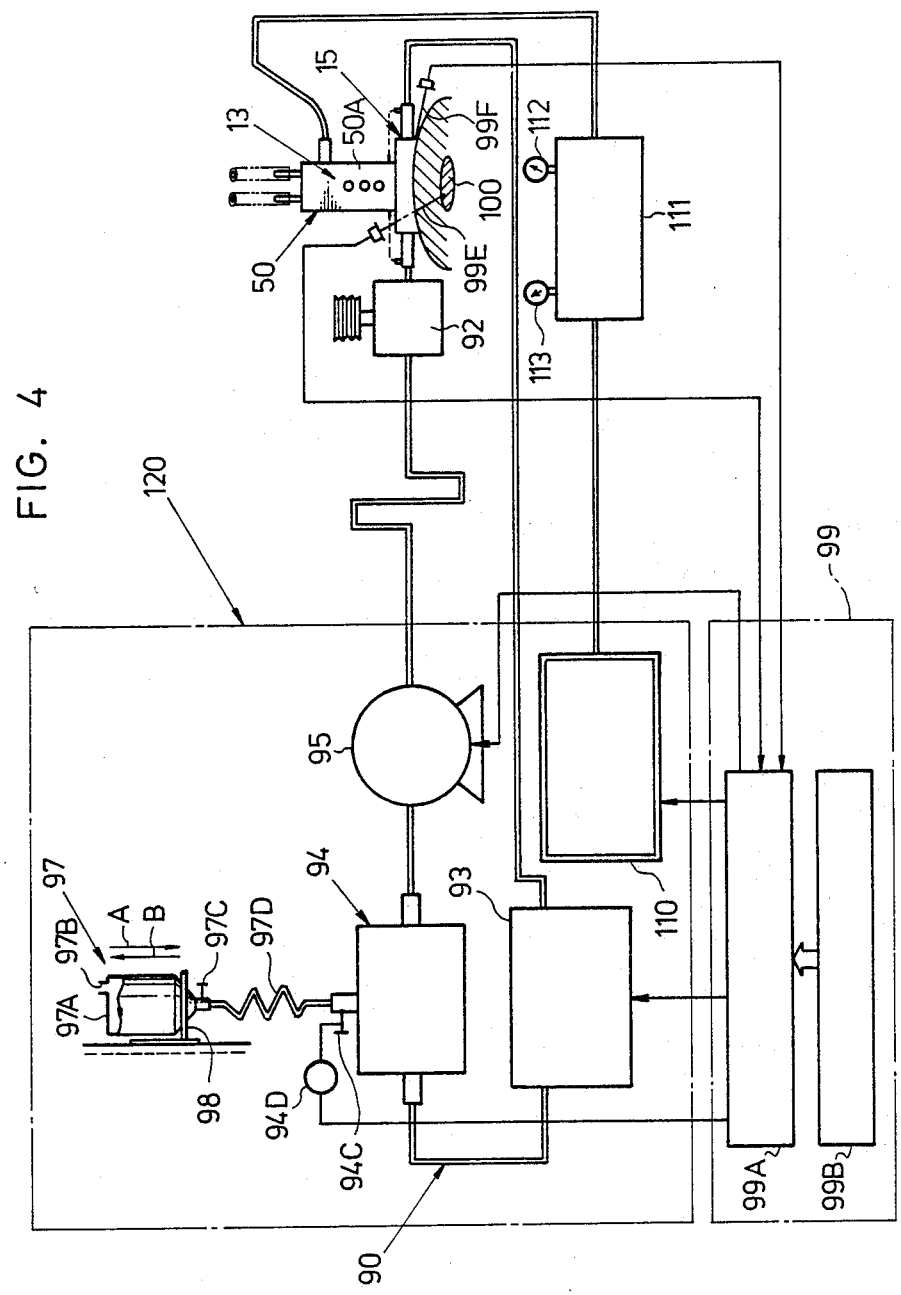
FIG. 4 is a block diagram showing the general arrangement including a coolant circulating mechanism and a control system.

More specifically, the surface cooling mechanism 15 is separate of the case body 10 in this embodiment. Namely, the surface cooling mechanism 15 is formed of a relatively soft insulating film member, and provided at one end thereof with a flow-in guide 31 for the coolant and at the other end with a flow-out guide 32 for the coolant. Branch paths 31A and 32A each having a relatively small diameter are provided on the flow-in and flow-out guides 31 and 32 for the coolant, respectively. These branch paths 31A and 32A are detachably communicated with the electromagnetic lens section 12 of the case body 10 of the applicator 50 as shown in FIGS. 4 and 5, to thereby form a deaerating mechanism 33. With this arrangement, air bubbles stangnant in the electromagnetic lens section 12 to be described hereunder are efficiently discharged.

Figure 8:
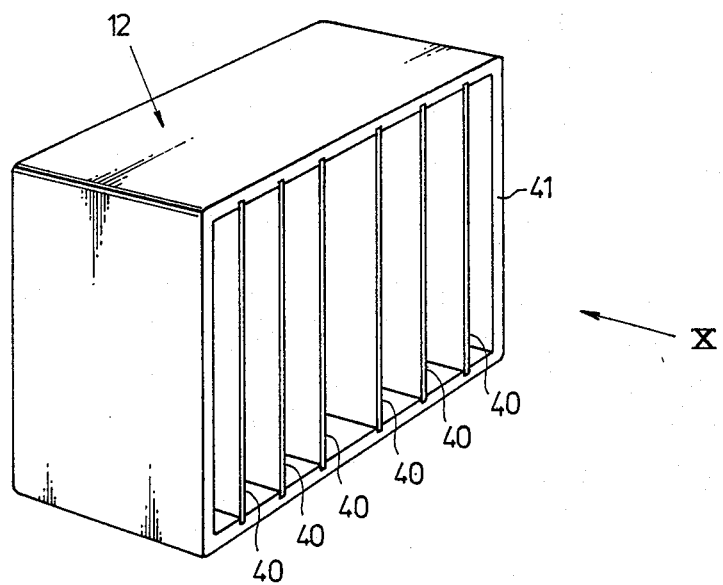
FIGS. 8 and 9 are perspective views showing the electromagnetic lens section used in FIG. 5.
Figure 9:
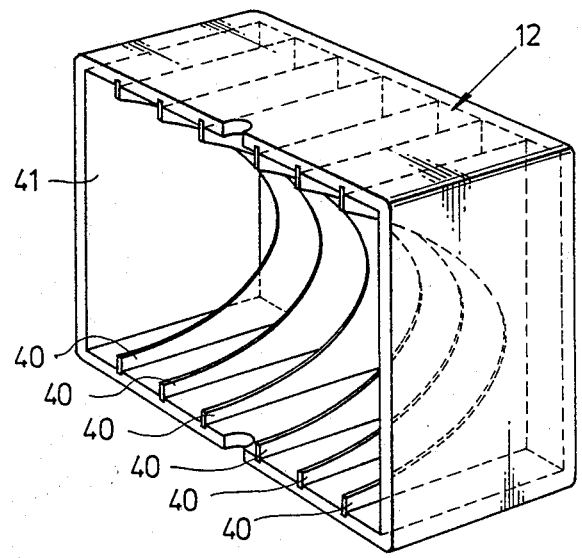

The electromagnetic lens section 12 provided on the right end portion of the case body 10 in FIG. 5 in this embodiment is formed to provide a box form wherein two opposing surfaces are open as shown in FIGS. 8 and 9, and the lens section 12 as a whole is detachably housed in the case body 10.

Figure 10:
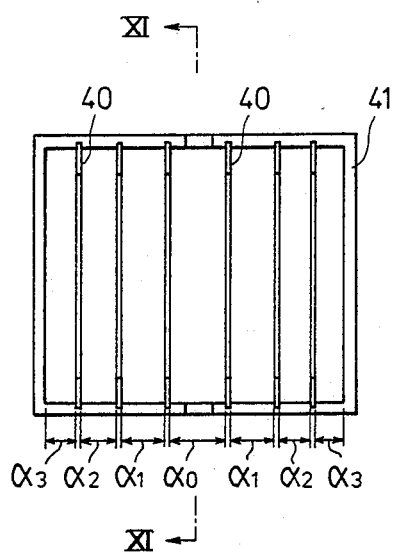
FIG. 10 is a front view in looking from an arrow X in FIG. 8.
Figure 11:
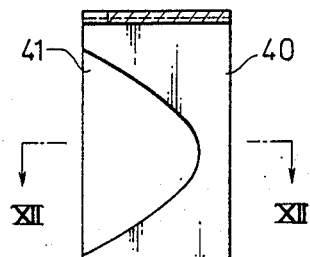
FIG. 11 is a sectional view taken along the line XI—XI.
Figure 12:
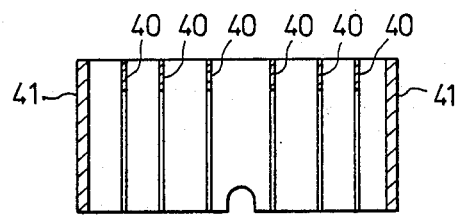
FIG. 12 is a sectional view taken along the line XII—XII in FIG. 11.
Figure 13:
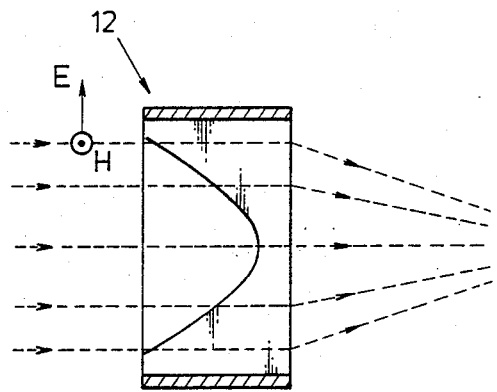
FIGS. 13 and 14 are explanatory views each illustrating the section of the electromagnetic lens section.
Figure 14:
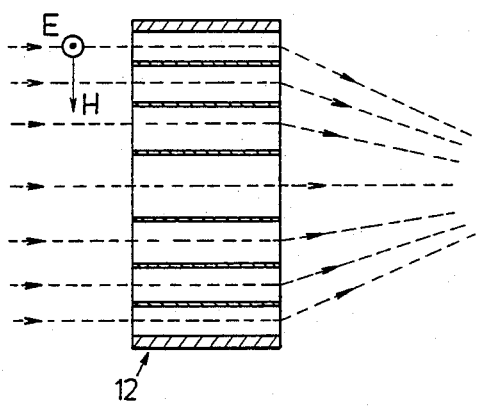

More specifically, the electromagnetic lens section 12 includes: a plurality of metal plates 40, 40, ... having the same dimensions; and a frame 41 engaging the top and bottom ends of these metal plates 40 is FIG. 8. These metal plates 40 are arranged such that an interval $a_0$ between the metal plates 40 at the center is the largest and intervals between the metal plates 40 are gradually decreased to be $a_1$, $a_2$ and $a_3$ (provided that $a_0 > a_1 > a_2 > a_3$) as the metal plates approach side walls 41A of the frame 41, as shown in FIG. 10. Thus, all of the metal plates 40 are arranged in one set so as to achieve a predetermined lens effect in one direction to the arriving electromagnetic waves as indicated by dot lines in FIG. 14.

Furthermore, each of the metal plates 40 has a form, in which the central portion thereof on the side of the electromagnetic wave feeding section 11 is cut away in an arcuate shape. With this arrangement, the predetermined lens effect can be achieved in the other direction to the same arranging electromagnetic waves as described above as shown in FIG. 13.

Furthermore, in FIG. 5, designated at 42 is a detachable sealing and insulating plate for engaging the electromagnetic lens section 12. In practice, scores of the detachable box-shaped electromagnetic lens sections 12 are previously prepared in accordance with affected portions, and suitable one is selectively used.

Detailed description will now be given of the above-described surface cooling mechanism 15, a coolant circulating mechanism 90 including the same, further, an electromagnetic wave oscillator 110 for delivering the electromagnetic waves into the applicator 50 and a control systems for all of these members.

In FIG. 4, the surface cooling mechanism 15 is connectingly provided at the coolant flow-in side thereof with fluid pressure buffer means 92 and at the coolant flow-out side thereof with coolant cooling means 93. The coolant liquid flowing out of the surface cooling mechanism 15 is cooled to a predetermined temperature by the cooling means 93, thereafter, deaerated by deaerating means 94 provided at the succeeding stage, thereupon, pressurized by a pressurizing pump 95, and thereafter, delivered again into the surface cooling mechanism 15 of the applicator 50 through the fluid pressure buffer means 92. The series of the coolant circulation systems, forming a closed loop, constitute a coolant circulating mechanism 90. Designated at 94C is an on-off valve controlled by a main control section 99A to be described hereunder to be on-off operated at predetermined time intervals. Further, denoted at 94D is a solenoid for directly driving the on-off valve 94C.

Further, a coolant feeding section 97 for feeding the coolant is connected to the coolant circulating mechanism 90 from the outside of the deaerating means 94.

This coolant feeding section 97 includes: a coolant feeding tank 97A; a feed port 97B opened at the top end portion of this coolant feeding tank 97A; an on-off valve 97C provided at the bottom end portion of the coolant feeding tank 97A; and means 98 for supporting the coolant feeding tank 98. In this coolant feeding section 97, the on-off valve 97C of the coolant feeding tank 97A is connected to the deaerating means 94 through an extendible piping 97D.

As a consequence, when the on-off valve 94C of the deaerating means 94 is opened due to biasing by the main control section 99A, air bubbles collected in the deaerating means 94 immediately rise and are discharged to the outside through the coolant feeding tank 97A.

Furthermore, the supporting means 98 can move in the vertical direction by a predetermined stroke as indicated by arrows A and B in FIG. 4. Consequently, in replacing the applicator 50 or parts of the applicator 50 with new one, the supporting means 98 is lowered to position the coolant feeding tank 97A beneath the applicator 50, and thereafter, a piping for the coolant is removed, whereby the applicator 50 or the parts thereof are replaced with new one, so that blow-out of the coolant can be avoided advantageously. Additionally, as the coolant, for example, pure water is desirable, however, in this embodiment, common water is used.

Furthermore, in this embodiment, as the coolant pressure buffer means 92, a bellows-shaped extendible device, the interior of which is communicated with a piping, is used. This belows-shaped extendible device, which is normally assumes a compressed form by its own elasticity, is used. Additionally, any mechanism equaling in function to this may replace the above-described device.

As an electromagnetic wave oscillator 110 for the applicator 50, a magnetron is practically used. An output therefrom is delivered to the applicator 50 through a directional coupler 111. In this case, the directional coupler 111 is provided with an output indicator 112 for indicating a rate of electromagnetic waves being currently delivered against the maximum output and a reflective wave indicating section 113 for indicating a rate of reflective electromagnetic waves. Consequently, when the reflective waves are large, the stub tuner mechanism 13 having the three stubs, of the applicator 50 is adjusted, so that the reflection level can be set to the lowest value.

Out of the above-described component members, mainly, the electromagnetic wave oscillator 110, the coolant cooling means 93, the deaerating means 94, the coolant feeding section 97 and the pressurizing pump 95 are housed in a main body 120 of apparatus, and, as necessary, the coolant pressure buffer means 92 and the directional coupler 111 are also housed in the main body 120 of apparatus.

In this embodiment, the coolant cooling means 93, the pressurizing pump 95 and the electromagnetic wave oscillator 110 are controlled by the main control section 99A of the control means 99 for the operation, respectively.

More specifically, constantly inputted into the main control section 99A are temperature information of portion 100 to be heated in the living body through a first thermometer 99E and temperature information of the surface of living body at a portion, into which the electromagnetic waves fall, through a second thermometer, respectively. Also inputted into the main control section 99A are cooling temperature of the surface of ling body, which is predetermined in accordance with each of patients, heating temperature of the portion to be heated in the living body, etc., and specific control steps through an input section 99B as the reference information for a specific control. For this, in the main control section 99A, first, an output from the electromagnetic wave oscillator 110 is controlled to be increased or decreased in accordance with values and steps previously inputted from the input section 99B and set, and further, the working levels of the pressurizing pump 95 and the cooling means 93 are controlled, whereby the temperature of the portion 100 to be heated for the treatment is constantly held within a predetermined range from 43° to 43.5° C. At the same time, in the main control section 99A, in order to prevent the surface of living body from being burnt, the coolant cooling means 93 and the pressurizing pump 95 are drivably controlled in accordance with the information from the second thermometer 99F.

While, as shown in FIGS. 2 and 3, the applicator holding means 60 is provided at the central portion of the U-shaped intermediate connecting portion 60C thereof with a support rod 61 and a portion of this support rod 61 is connected to a forward end arm 71 of a supporting mechanism 70 through a connecting mechanism 62 (Refer to FIG. 2).

More specifically, the connecting mechanism 62 includes: a fixing member 62A formed at the forward end thereof with external threads; and a connecting member 62B formed with internal threads threadably coupled to this fixing member 62A. This connecting member 62B engages the support rod 61 of the aforesaid U-shaped applicator holding means 60, said support rod 61 being permitted in rotation and reciprocatory motion in the axial direction. In this case, the rotation of the support rod 61 is permitted only when the threaded portion of the connecting mechanism 62 is loosened.

An urging mechanism 80 for constantly urging the applicator holding means 60 downwardly in FIG. 2 is provided between this connecting mechanism 62 and the applicator holding means 60. In this embodiment, a coil spring is used as this urging mechanism 80.

Because of this, the applicator 50 can be brought into abutting contact with the cooling mechanism 15, so that the contact surfaces can be abutted against each other under a constantly suitable urging force.

The supporting mechanism 70 includes: a support arm portion 72; a support post 73 for supporting this support arm portion 72; a base board 74 being movable and planted therein with this support post 73; a weight 75 solidly secured to this base board 74; a suspended arm portion 76 engaged with one end portion of the support arm portion 72; a forward end arm 71 connected to the forward end portion of this suspended arm portion 76; and a balancer 77 provided at the other end portion of the support arm portion 72.

The support arm portion 72 is formed at the substantially central portion thereof with a fixed portion 72A. The support arm portion 72 is fixed to the support post 73 at this fixed portion 72A through fixing means 72B, and, as necessary, the fixing means 72B is loosened, so that the support arm portion 72 can rotate about the support post 73 as indicated by an arrow G or vertically move as indicated by an arrow H.

The balancer 77 provided at the other end of the support arm portion 72 is used for keeping the balance between the arm portions. This balance 77 can move reciprocatingly on the support arm portion 72 in a direction indicated by an arrow K by loosening a fixing knob 77a, and, can be fixed to a desirable position by tightening the fixing knob 77A.

Further, the suspended arm portion 76 provided at one end portion of the arm portion 72 can reciprocatingly move on the support arm portion 72 by loosening the fixing knob 76A as being the fixing knob in a direction indicated by an arrow M, and can rotate on the support arm portion 76 by loosening a lever 76B on the side of the support arm portion 72 in a direction indicated by an arrow N. Similarly, the forward end arm portion 71 can be directly rotated at a portion connected to the suspended arm 72 by loosening a lever 71B in a direction indicated by an arrow P.

Thus, the applicator 50 can be moved to a desired position and substantially fixed in a desirably inclined state by the applicator holding means 60, the supporting mechanism 70 and the urging mechanism 80. Even a slight movement of the patient can be followed relatively easily through the action of the urging mechanism 80, to thereby hold a suitable contact with the patient. Further, the surface cooling mechanism 15 is separate from the case body 10, whereby the burden of the supporting mechanism 70 is considerably reduced, so that the general balance can be maintained. As a result, in performing hyperthermia, the handling of the apparatus as a whole can be very easy and the preparation works can advantageously proceed on accurately for a short period of time.

Additionally, in the above embodiment, the surface cooling mechanism 15 is generally formed of the flat-shaped soft member, so that the urging mechanism 80 can be dispensed with for a patient having a small movement.

The Second Embodiment

The second embodiment of the present invention will hereunder be described with reference to FIGS. 15 to 20. Here, the same reference characters will be used to designate the same or similar component parts in the drawings as used in the first embodiment.

Figure 15:
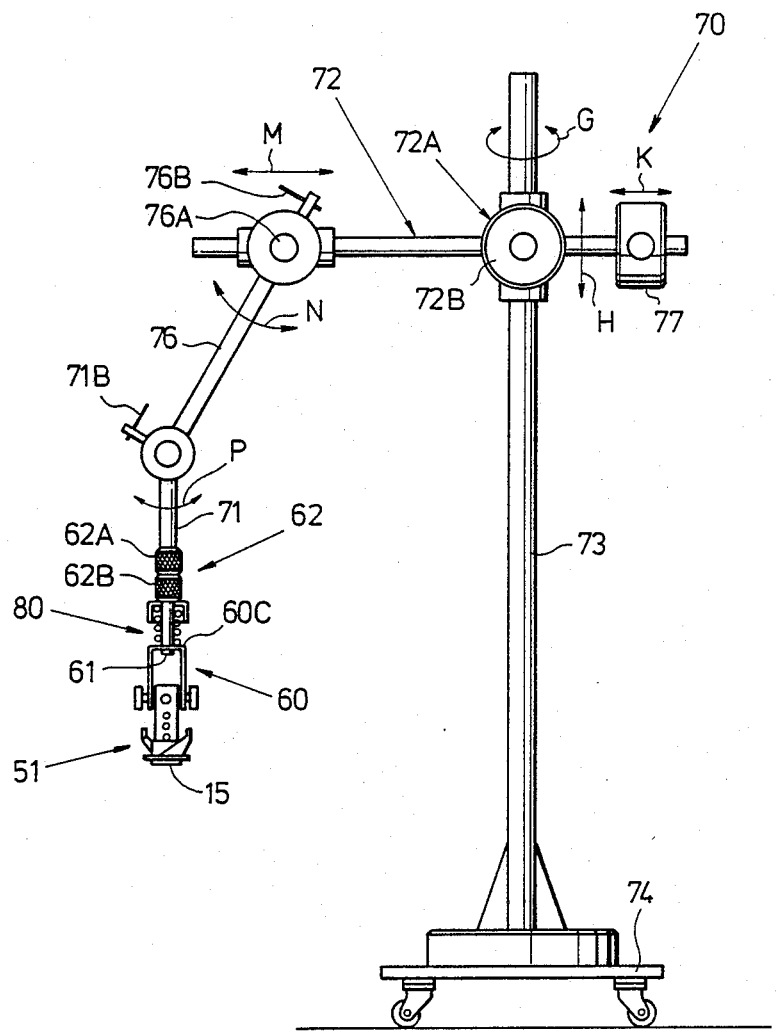
FIG. 15 is a front view showing the supporting mechanism in a second embodiment.

First, in FIG. 15, designated at 51 is an applicator, 60 applicator holding means and 70 a supporting mechanism.

Similarly to the first embodiment, the applicator 51 is erectingly and rotatably engaged with the applicator holding means 60 through engaging knobs 60E and 60F. Denoted at C and D are rotating directions in that case. In this case, the central portions of the engaging knobs 60E and 60F are extended inwardly and formed at ends thereof with threaded portions, not shown, respectively. These threaded portions extend through through-holes, not shown, of U-shaped end portions 60A and 60B of the applicator holding means 60, and then, threadably coupled to threaded holes 10K of engageable pieces 10G and 10H (Refer to FIG. 19) provided at opposite sides of the applicator 51. Consequently, the applicator 51 is solidly secured to the applicator holding means 60 through the action of the engaging knobs 60E and 60F thereof in such a manner that the opposite sides of the applicator 51 is clamped by the bent end portions 60A and 60B of the applicator holding means 60.

Figure 17:
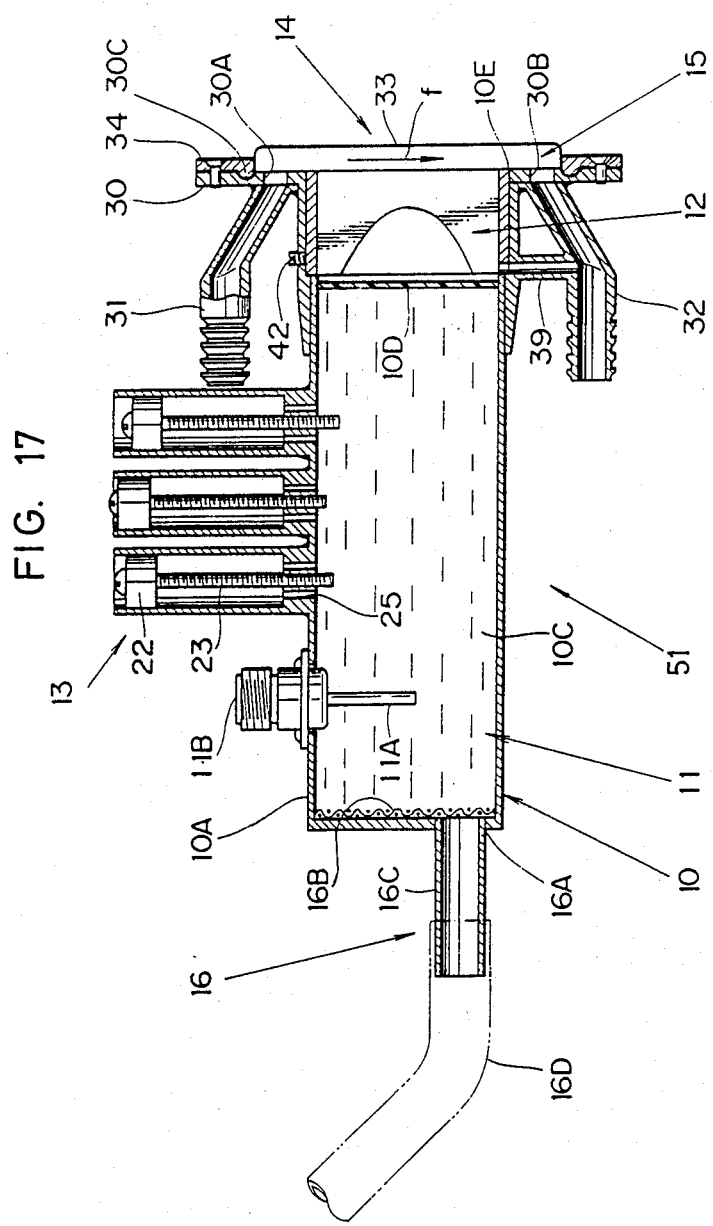
FIG. 17 is a sectional view showing the applicator portion in the second embodiment.
Figure 18:
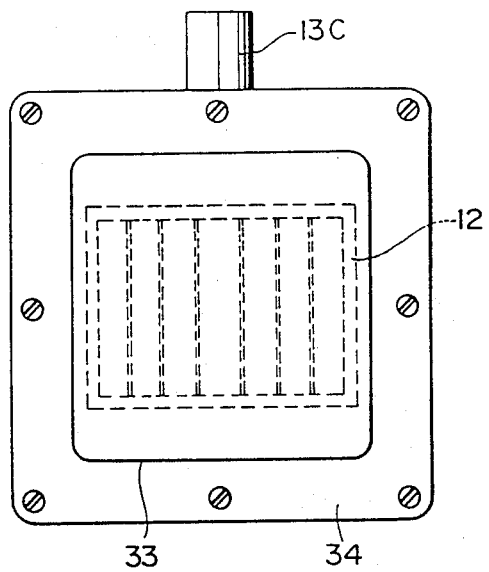
FIG. 18 is a right side view of FIG. 17.
Figure 19:
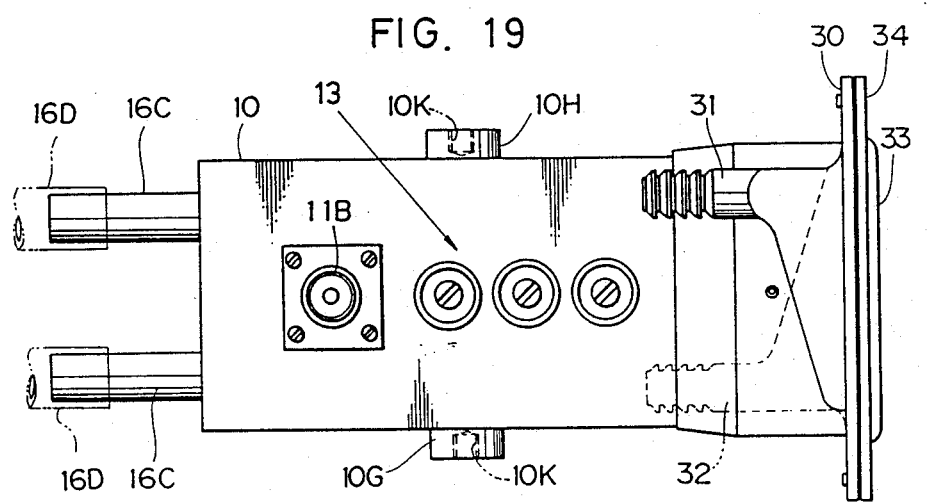
FIG. 19 is a plan view of FIG. 17.
Figure 20:
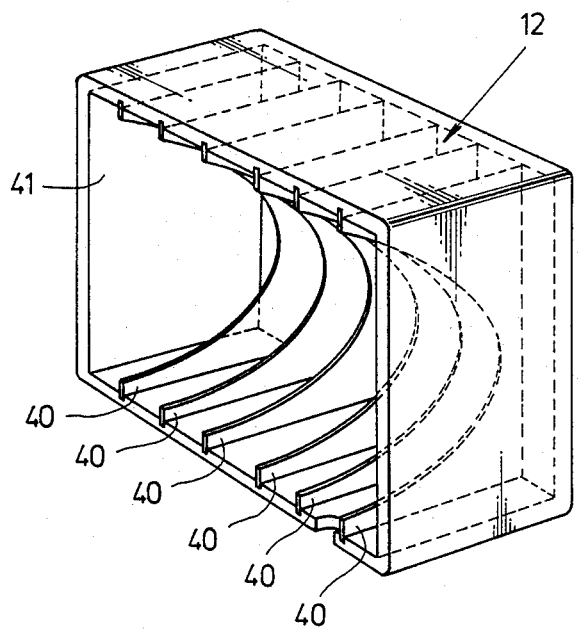
FIG. 20 is a perspective view showing the lens portion used in the applicator in FIG. 17.

As specifically shown in FIGS. 17 to 19, the applicator 51 differs from the first embodiment in that the case body 10 is formed integrally with the cooling mechanism 15. Namely, the right end portion of the electromagnetic lens section 12 is open to form an electromagnetic wave radiating end section 14, which is provided with a cooling mechanism 15 for cooling the surface of living body in a manner to cover the electromagnetic wave radiating end section 14 from the outside.

The cooling mechanism 15 is formed to provide a flat shape to efficiently cool the surface of living body.

More specifically, the cooling mechanism 15 includes: an engaging base plate 30 integrally fixed to the case body 10; a rectangular coolant flow-in port 30A formed at one end portion of this engaging base plate 30; a rectangular coolant flow-out port 30B formed at the other end portion of the engaging plate 30 as opposed to the flow-in port 30A; an insulating film water preventive groove 30C cuttingly formed, surrounding these coolant flow-in and flow-out ports 30A and 30B, and an opening 10E of the electromagnetic wave radiating end section 14; coolant guides 31 and 32 which are connected and fixed to the coolant flow-in and flow-out ports 30A and 30B respectively; a flat-shaped insulating film member 33 provided for covering the generally entire surface of the electromagnetic wave radiating end section 14; and a frame place 34 detachably mounted to the engaging base plate 30, making the outer periphery of the insulating film member 33. Out of the above-mentioned members, the insulating film member 33 is formed of a film-like dielectric material being of a tray shape, convex outwardly and opening inwardly and low in attenuation of the electromagnetic waves. The coolant which flowed in through the coolant flow-in port 30A flows inside the insulating film member 33 and delivered to the coolant flow-out port 30B as indicated by an arrow f in FIG. 15, during which the coolant can cool the surface of living body efficiently through the insulating film member 33.

Further, as air bubble escaping means communicated with the coolant guide 32 for the coolant flow-out, a piping 39 having a relatively small diameter is provided on the electromagnetic lens section 12 on the side of the electromagnetic wave feeding section 11, so that the air bubbles produced during the treatment can be directly sucked to the outside through the coolant guide 32 by negative pressure due to the flow of the coolant.

Figure 16:
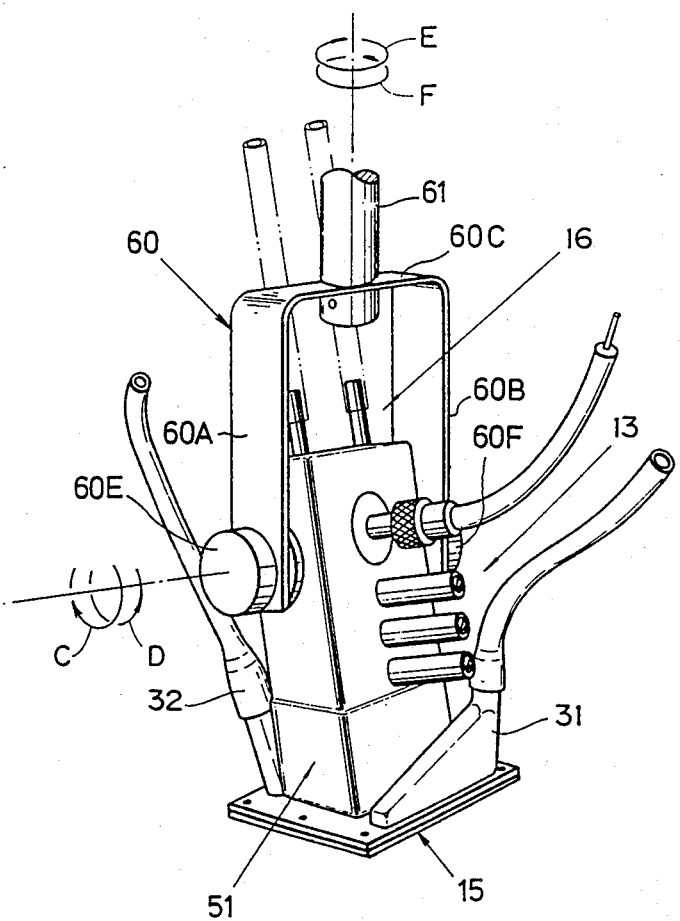
FIG. 16 is an enlarged perspective view showing the applicator holding means portion in FIG. 15.

On the other hand, as shown in FIGS. 15 and 16, the applicator holding means 60 is provided at the central portion of the U-shaped intermediate connecting portion 60C thereof with the support rod 61 which is connected to the forward arm 71 of the support mechanism 70 through the connecting mechanism 62 (Refer to FIG. 15).

Other respects in the construction are identical with those in the first embodiment.

With this arrangement, the second embodiment has the functions and effects substantially equal to those in the first embodiment, and advantageously, necessity of labor for providing the cooling mechanism is eliminated, and the workability can be improved accordingly.

What is claimed is:

1. A heating apparatus for inducing hyperthermia, comprising: an applicator for focusing and outputting electromagnetic waves; applicator holding means for erectingly and rotatably engaging and holding said applicator and a supporting mechanism for supporting said applicator holding means; and an additional mechanism operatively associated with said supporting mechanism for urging said applicator in a predetermined direction.

2. A heating apparatus for inducing hyperthermia, comprising: an applicator having an output end for focusing and outputting electromagnetic waves to a portion of a patient undergoing treatment for heating such portion; applicator means for erectingly and rotatably engaging and holding said applicator; and a mechanism for supporting said applicator holding means; a mechanism for cooling the outer surface of said portion to be heated and a coolant circulating mechanism including a pressurizing pump for effecting the flow of coolant in and out of said mechanism which is located at the electromagnetic wave output end of said applicator, and deaerator means for deaerating said coolant.

3. A heating apparatus for inducing hyperthermia, comprising: an applicator having an output end for focusing and outputting electromagnetic waves to a portion of a patient undergoing treatment for heating such portion; applicator holding means for erectingly and rotatably engaging and holding said applicator; and a mechanism for supporting said applicator holding means; a mechanism for cooling the outer surface of said portion to be heated and a coolant circulating mechanism including a pressurizing pump for effecting the flow of coolant in and out of said mechanism which is located at the electromagnetic wave output end of said applicator; and fluid pressure buffer means located between the pump and the applicator for reducing coolant pressure when the coolant delivered into said cooling mechanism is abnormally pressurized.

4. A heating apparatus for inducing hyperthermia, comprising: an applicator having an output end for focusing and outputting electromagnetic waves to a portion of a patient undergoing treatment for heating such portion; applicator holding means for erectingly and rotatably engaging and holding said applicator; and a mechanism for supporting said applicator holding means; a mechanism for cooling the outer surface of said portion to be heated and a coolant circulating mechanism including a pressurizing pump for effecting the flow of coolant in and out of said mechanism which is located at the electromagnetic wave output end of said applicator; and a coolant feed section at the inlet to the pump, said coolant feeding section being vertically movable on supporting means.

5. A heating apparatus for inducing hyperthermia, comprising: an applicator for focusing and outputting electromagnetic waves; applicator holding means for erectingly and rotatably engaging and holding said applicator; and a mechanism for supporting said applicator holding means, said apparatus further comprising an electromagnetic wave oscillator section provided on a main body of apparatus for producing and outputting the electromagnetic waves for said applicator; a coolant circulating mechanism including a surface cooling mechanism for cooling the surface of a living body irradiated by said electromagnetic wave oscillator to the optimally heating state; and control means separate from the main body of apparatus for controlling operation of said coolant circulating mechanism.

6. A heating apparatus for inducing hyperthermia, comprising: an applicator having an output end for focusing and outputting electromagnetic waves to a portion of a patient undergoing treatment for heating such portion; applicator holding means for erectingly and rotatably engaging and holding said applicator; a mechanism for supporting said applicator holding means; and a surface cooling mechanism located at the electromagnetic output end of said applicator, but separate from said applicator for cooling the outer surface of said portion.

7. A heating apparatus according to claim 1 wherein said applicator has orthogonal first and second axes for adjustment, and said applicator holding means is constructed and arranged so that said applicator is selectively adjustable to a predetermined angular position relative to said orthogonal first and second axes.

8. A heating apparatus according to claim 7 wherein said additional mechanism includes a spring member that biases the applicator in the direction of one of said axes.

9. A heating apparatus according to claim 7 including a connection member interposed between said support mechanism and said applicator holding means, said connecting member including coaxial members collectively operable for fixing the angular position of the applicator relative to the axis of the coaxial members.

10. A heating apparatus according to claim 9 wherein said applicator holding means includes a support rod operatively associated with and coaxial with the coaxial members for establishing the maximum axial position of the applicator relative to the connection member.

11. A heating apparatus according to claim 10 wherein said applicator holding means includes a U-shaped portion having a base connected to the support rod and a pair of spaced arms establishing an axis perpendicular to the axis of said coaxial members, and means for adjusting the angular position of the applicator relative to the axis established by said arms.

12. A heating apparatus according to claim 11 including a spring interposed between the base of said U-shaped portion and said coaxial member for resiliently urging the applicator away from said coaxial members.

13. A heating apparatus according to claim 12 wherein said support mechanism is adjustable for adjusting the spatial position of said applicator.

14. A heating apparatus according to claim 2 wherein said deaerator means includes a deaerator located at the inlet to said pump, and a selectively operable valve on the top of said deaerator for selectively venting said deaerator.

15. A heating apparatus according to claim 14 wherein the deaerator means includes a vented deaerator tank connected to the outlet of said valve, said tank being vertically movable relative to said applicator.

16. A heating apparatus according to claim 2 wherein said applicator includes an electromagnetic lens section at the electromagnetic wave output end of said applicator for focusing the electromagnetic waves outputted by said applicator, means associated with said surface cooling mechanism for cooling said lens, and deaerator means associated with said lens for deaerating the latter.

17. A heating apparatus according to claim 16 wherein said deaerator means includes a coolant conduit located adjacent the interface between the electromagnetic output end of the applicator and the lens for causing the flow of coolant through the lens to sweep bubbles from said interface.

18. A heating apparatus according to claim 6 comprising a coolant loop that includes said surface cooling mechanism, said loop comprising coolant reservoir means containing coolant, a pump for effecting the exchange of coolant between the reservoir means and the surface cooling mechanism, and a selectively operable coolant cooler for selectively cooling the coolant, and a control section responsive to the temperature of said coolant at the outlet side of said surface cooling mechanism, and responsive to the internal temperature of said portion for controlling the operation of said pump and the operation of said coolant cooler.

* * * * *

UNITED STATES PATENT AND TRADEMARK OFFICE
CERTIFICATE OF CORRECTION

PATENT NO. : 4,891,483

DATED : January 2, 1990

INVENTOR(S) : M. KIKUCHI et al.

It is certified that error appears in the above-identified patent and that said Letters Patent is hereby corrected as shown below:

Column 2, line 32, insert ---forming--- after "applicator".

Column 2, line 42, change "XI;" to ---XI in FIG. 10;---.

Column 3, line 8, change "hoding" to ---holding---.

Column 4, line 39, change "stangnant" to ---stagnant---.

Column 5, line 39, change "98" to ---97A--- after "tank".

Column 5, line 65, delete "is".

Column 6, lines 32/33, insert ---99F--- after "thermometer".

Column 6, line 35, change "ling" to ---the living---.

Column 7, line 36, change "77a" to ---77A---.

Signed and Sealed this

Tenth Day of December, 1991

Attest:

HARRY F. MANBECK, JR.

*Attesting Officer*     *Commissioner of Patents and Trademarks*